United States Patent [19]
Voll

[11] 3,948,091
[45] Apr. 6, 1976

[54] APPARATUS FOR DETERMINING THE PROPERTIES OF METALLIC MATERIALS

[75] Inventor: Hubert Paul Voll, Ougree, Belgium

[73] Assignee: Centre de Recherches Metallurgiques - Centrum voor Research in de Metallurgie, Brussels, Belgium

[22] Filed: May 21, 1974

[21] Appl. No.: 471,898

[30] Foreign Application Priority Data
May 24, 1973  Belgium.................. 800013

[52] U.S. Cl. .................................... 73/95
[51] Int. Cl.² .......................................... G01N 3/08
[58] Field of Search ........................................... 73/95

[56] References Cited
UNITED STATES PATENTS

| | | |
|---|---|---|
| 3,140,601 | 7/1964 | Weyland ................................. 73/95 |
| 3,379,054 | 4/1968 | Folweiler ................................ 73/95 |
| 3,400,576 | 9/1968 | Siciliano ................................. 73/95 |
| 3,533,284 | 10/1970 | Slemmons et al. ..................... 73/95 |
| 3,733,049 | 5/1973 | Hove ....................................... 79/95 |
| 3,836,757 | 9/1974 | Nachtigal ................................ 79/95 |

Primary Examiner—Richard E. Aegerter
Assistant Examiner—Willis Little
Attorney, Agent, or Firm—Holman & Stern

[57] ABSTRACT

The apparatus includes a machine for subjecting a test-piece of superplastic material to a tensile test using a mobile member entraining one end of the test-piece and exerting traction on the test-piece. The mobile member is subjected to successive displacements whose speed and duration are controlled. The force applied to the test-piece and its length are measured as a function of time.

2 Claims, 3 Drawing Figures

APPARATUS FOR DETERMINING THE PROPERTIES OF METALLIC MATERIALS

The present invention relates to apparatus for determining the properties of metallic materials, particularly the modulus of elasticity of these materials, using a computer-controlled tensile testing machine.

Various tensile testing machines have already been introduced which are computer-controlled to rapidly, continuously, and automatically determine the following properties of metallic materials:
1. the conventional elastic limit (proof stress) at a given elongation, for example 0.2%,
2. the upper and lower elastic limits,
3. the length of the yield range,
4. the normal anistropic coefficient of plastic strain (r),
5. the work-hardening coefficient (n),
6. rational elongation corresponding to maximum load,
7. load at fracture.

A tensile testing machine used to establish the above properties may be horizontal or vertical, of conventional design (for laboratory tests) or of special design to carry out tests in workshops for example to control manufacture in situ. The computer controlling the tensile testing machine may be analog, digital, or even hybrid.

The metallic materials under study may be ferrous materials, particularly steel, or non-ferrous materials. The properties determined are not only the normal behavior of the materials in the elastic and plastic ranges but also special behavior, for example superplasticity.

A particularly interesting mechanical property which is the origin of a large number of other properties is the longitudinal modulus of elasticity or Young's modulus E, given by the equation $$\sigma = E \cdot \epsilon$$

in which $\sigma$ is the load (N) to which the material is subjected, divided by its cross-sectional area ($\Omega$), thus $$\sigma = \frac{N}{\Omega}$$

and $\epsilon$ is the proportional elongation, i.e. the ratio of elongation $\delta$ to the length $l$ of the material $$\epsilon = \frac{\delta}{l}$$

The more rigid the material the greater the modulus E.

When tensile tests are carried out on ordinary steels at ambient temperature, the modulus E is predetermined at a value, about 21,000 kg/mm², which remains practically constant throughout the test.

When special steels or non-ferrous metals are studied tensile tests are carried out at widely differing temperatures, which means that the modulus E can vary greatly. In these circumstances, the value of the modulus E cannot be predetermined but must be determined on each occasion.

The object of the present invention is apparatus which makes it possible to accurately, rapidly, and automatically determine the modulus of elasticity E irrespective of the metallic material under study and irrespective of the temperature and tensile test speed conditions.

The invention will be described with reference to the accompanying drawings, in which.

The invention is based on the following considerations.

Figure 1:
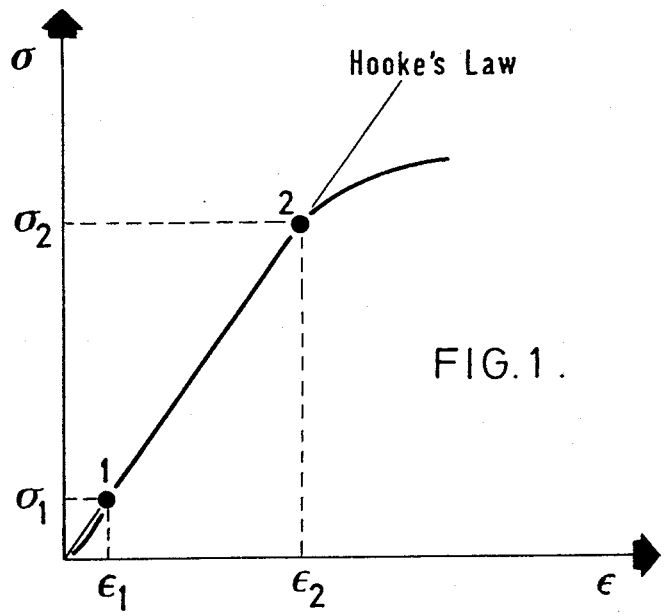
FIG. 1 is a stress-strain diagram.

In the stress-strain diagram (FIG. 1) which shows the proportional elongations ($\epsilon$) as abscissae and the stresses ($\sigma$) as ordinates, the elastic range is represented by Hooke's law, which states that the stress is proportional to the strain, and in the diagram is a straight line. The modulus E is given by the gradient of the straight line.

The straight line must therefore be established before determining the modulus E.

It is well known that, at the start of the tensile test, the test-piece is not stressed in perfect agreement with Hooke's law, due to slight displacement of the jaws and alignment of the test-piece. After this stage, the straight line is established between the point 1 ($\sigma_1, \epsilon_1$) at which the stress becomes proportional to the strain and the point 2 ($\sigma_2, \epsilon_2$) at which the graph departs from Hooke's law; these two points are not accurately known. Young's modulus (E) is obviously equal to $$\frac{\sigma_2 - \sigma_1}{\epsilon_2 - \epsilon_1} = \frac{\Delta\sigma}{\Delta\epsilon}$$

and the modulus (E) is determined by calculating the gradient, i.e. calculating the maximum value of $$\frac{\Delta\sigma}{\Delta\epsilon}.$$

This calculation is not just a matter of simply finding the maximum of the various terms $$\frac{\Delta\sigma_i}{\Delta\epsilon_i},$$

since the value established in this way would be erroneous due to the lack of accuracy in the measuring devices and in any processing of the load and elongation signals, being inherent in the functioning of sensors, and due to the brevity of the proportional elongation in the elastic range compared with the total elongation to fracture.

The Applicant has developed an algorithm which makes it possible to systematically calculate the straight line using a computer; this algorithm overcomes the drawbacks faced in calculations currently carried out.

Figure 2:
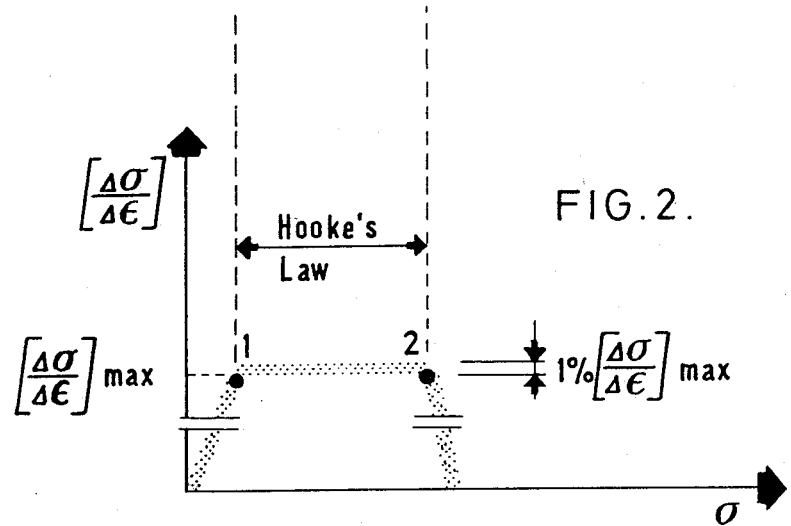
FIG. 2 is a graph of the first derivative of the stress with respect to strain.

The algorithm corresponds to the following operations:

a. calculations of the various terms $$\frac{(\Delta \sigma_i)}{\Delta \epsilon_i}$$

from the successive values provided by the sensors of the stress ($\Delta \sigma_i$) and elongation $$\frac{\Delta \sigma_i}{\Delta \epsilon_i} = \frac{\sigma_i - \sigma_i - 1}{\epsilon_i - \epsilon_i - 1}$$

b. determination of the maximum value of the various terms $$\frac{\Delta \sigma}{\Delta \epsilon} \text{ i.e. } \frac{(\Delta \sigma)}{\Delta \epsilon}\text{max}$$

c. determination of all the other terms $$\frac{(\Delta \sigma_i)}{\Delta \epsilon_i}$$

not differing from the term $$\frac{(\Delta \sigma)}{\Delta \epsilon}\text{max}$$

by more than a small amount, e.g. 1%, within the limits of experimental error, thus enabling the gradient of the straight line to be plotted as a function of the stress $\sigma$, (FIG. 2);

d. use of the representative signal of the gradient of the line as a function of the stress $\sigma$ to establish the other properties of metallic materials, for example the elastic limit and the elastic and plastic strain ranges using known methods.

According to one mode of use of the algorithm, the modulus of elasticity (E) of the metallic material is determined in the following way:

a. the various terms $$\frac{(\Delta \sigma_i)}{\Delta \epsilon_i}$$

which define the gradient of the line as a function of the stress ($\sigma$) are considered to correspond to the points situated along a straight line and the stresses ($\sigma_1, \sigma_2$) at the first and last of these points, which comprise the extremities (1 and 2) of the straight line (along the 0 scale), are determined and the corresponding strains ($\epsilon_1, \epsilon_2$) are recorded;

b. the modulus of elasticity is calculated using the formula $$E = \frac{\sigma_2 - \sigma_1}{\epsilon_2 - \epsilon_1}.$$

According to a second mode of use of the algorithm, in order to reduce the time of calculation, which may be critical if the test is carried out at high speed, the various terms $$\frac{\Delta \sigma_i}{\Delta \epsilon_i}$$

are calculated by adopting constant step-wise variations of stress ($\Delta \sigma_i$) or elongation ($\Delta \epsilon_i$).

Having described the principles used to obtain the desired results, the apparatus according to the present invention which makes it possible to embody the operations described above and to efficiently obtain the anticipated results, will now be illustrated.

The apparatus comprises: a machine for subjecting a suitable test-piece to a tensile stress using a mobile member, such as a cross-piece, entraining one of the ends of the test-piece, exerting traction on the test-piece; means for subjecting the said mobile member to controlled displacements; means for measuring the force applied to the test-piece as a function of time at any moment during the test; means for measuring the length of the test-piece as a function of time at any moment during the test.

An advantageous embodiment of the apparatus further comprises a computer which:

a. immediately processes the data supplied by the above-mentioned measuring means, in accordance with the information in the specification and particularly in accordance with the formulae, b. programs the movement of the mobile member in accordance with the information in the specification, c. provides the results, i.e. the value of the modulus of elasticity of the tested material, either in digital or analog form.

Figure 3:
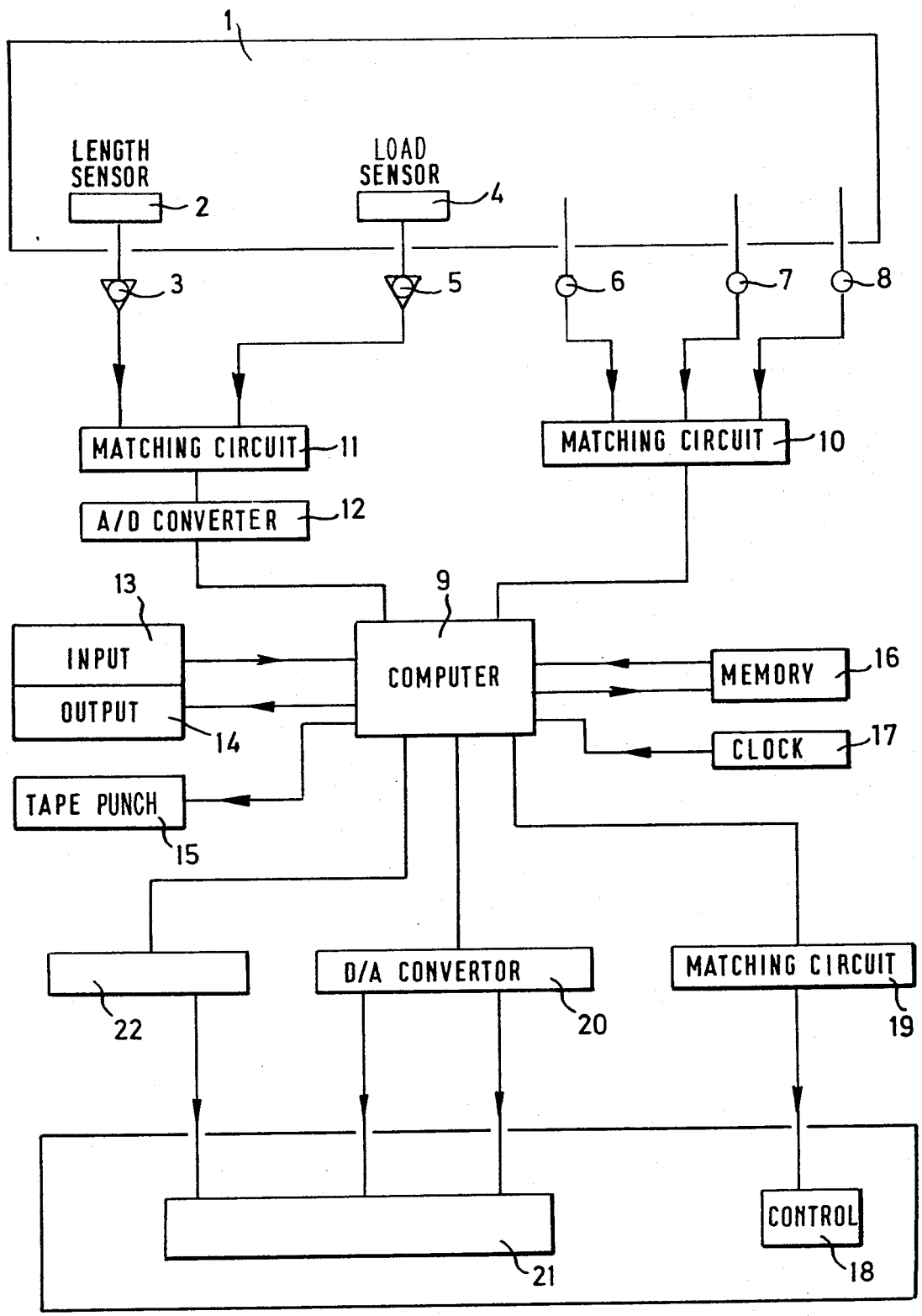
FIG. 3 is a block diagram of one embodiment of apparatus according to the invention.

A preferred embodiment of the apparatus comprises (FIG. 3): a sensor 2 which measures the length of the test-piece during the test; an amplifier 3 which amplifies the signal emitted by the sensor 2; a sensor 4 which measures the load applied to the test-piece; a variable gain amplifier 5 which amplifies the signal emitted by the sensor 4; a deviation calibration and correction device with control buttons 6; a speed selector 7 (providing nine speeds, for example) for the mobile cross-piece; a member 8 which shows the stop position or direction of movement of the cross-piece; three matching circuits 10, 11, 19; an analog/digital (A/D) converter 12; a digital/analog (D/A) converter 20; a central computer unit 9; a data printer 13; a result printer 14; a tape punch 15; a memory 16; a real time graduated clock 17; a control circuit 18 which controls the movements of the mobile cross-piece; the whole assembly having the following electrical connections:

a. 2 – 3 – 11 – 12 – 9
b. 4 – 5 – 11 – 12 – 9
c. 6 – 10 – 9
d. 7 – 10 – 9
e. 8 – 10 – 9
f. 13 – 9
g. 14 – 9
h. 15 – 9; 16 – 9; 17 – 9
i. 20 – 9
j. 18 – 19 – 9, which allow a and b: the supply of the signals from the two sensors into the central unit 9, c: checking and correction of the deviation of sensor 4 and its amplifier 5, d: control of the position and regulation of the speed selector;

e: control of the cross-piece state f and g inputting of data and reception of the test results, h: printing the results on tape, "memory - central unit" link, time keeping, i: outputting the results in analog form, j: control of the movements and stopping of the cross-piece from the central unit, in accordance with the program fed into it.

The apparatus operates as follows: the test-piece is fitted into the tensile testing machine 1. The computer unit 9 is fed with data (from the printer 13) including the cell calibration signal, before the test. Using the member 8 the operator orders the computer to start the motion of the cross-piece; the computer verifies that all the data have been fed in and then uses the control circuit 18 to start the test. During the test the measured parameters (length of the test-piece), load applied, (speed of cross-piece) are continuously recorded and calculations which establish the modulus E are made as shown in the specification, particularly the equations therein. The end of the test is detected using a predetermined stop parameter. The printer 14 then supplies the test results, their representative curves are obtained using 20 – 21 – 22.

I claim:

1. Apparatus for determining the modulus of elasticity of a metallic material, which comprises:

a machine for subjecting a testpiece of metallic material to a tensile test, said machine including mobile member means engaging one of the ends of said testpiece for exerting traction thereon;

means applied to said mobile member means for subjecting same to controlled displacements whereby traction is exerted on said test-piece in controlled steps;

means for measuring the force applied to said test-piece by said mobile member means as a function of time and for providing data indicative thereof;

means for measuring the length of said test-piece as a function of time and for providing data indicative thereof; and a computer which is connected to said mobile member controlled displacement subjecting means, said force measuring means and said length measuring means, said computer including means for processing said data from said force and length measuring means in accordance with preprogrammed formulas stored therein to provide an output indicative of the modulus of elasticity of said metallic material, said computer further including means for providing control signals for controlling the movement of said mobile member controlled displacement subjecting means;

said length measuring means comprising a length sensor which measures the length of said test-piece and an amplifier connected to receive the output of said length sensor;

said force measuring means comprising a load sensor which measures the load applied to said test-piece and a variable gain amplifier connected to receive the output from said load sensor; and wherein said apparatus further comprises:

a first matching circuit connected to receive the outputs from said amplifier and said variable gain amplifier;

an analog-to-digital converter connected to receive the output from said first matching circuit and to deliver an input to said computer;

a deviation calibration and correction device connected to said machine, a speed selector connected to said machine, an indicating member connected to said machine for providing an output indicative of the stop position and direction of movement of said test-piece, and a second matching circuit whose inputs comprise the outputs from said correction device, said speed selector, and said indicating member, and whose output is connected to said computer.

2. The apparatus as set forth in claim 1, further comprising:

a digital-to-analog converter for receiving said output from said computer;

display means connected to receive the output from said digital-to-analog converter for plotting said output in analog form;

an input printer and an output printer connected to said computer;

a memory and a clock connected to said computer; and wherein said mobile member controlled displacement means comprises a control circuit connected to said computer through a third matching circuit.

* * * * *